US007290436B2

(12) United States Patent
Olde Weghuis et al.

(10) Patent No.: US 7,290,436 B2
(45) Date of Patent: Nov. 6, 2007

(54) DEVICE FOR MEASURING THE STATIC AND/OR DYNAMIC FRICTION COEFFICIENT OF A SURFACE

(75) Inventors: Marinus Hendrikus Olde Weghuis, Oldenzaal (NL); Gerben Christiaan Bierma, Enschede (NL); Hendrik Hazenberg, Enschede (NL); Ingo Wynand Witbreuk, Oldenzaal (NL)

(73) Assignee: Ten Cate Thiolon B.V., Re Nijverdal (NL)

( * ) Notice: Subject to any disclaimer, the term of this patent is extended or adjusted under 35 U.S.C. 154(b) by 81 days.

(21) Appl. No.: 10/535,282

(22) PCT Filed: Sep. 16, 2003

(86) PCT No.: PCT/NL03/00639

§ 371 (c)(1),
(2), (4) Date: Feb. 16, 2006

(87) PCT Pub. No.: WO2004/051239

PCT Pub. Date: Jun. 17, 2004

(65) Prior Publication Data

US 2006/0130556 A1 Jun. 22, 2006

(30) Foreign Application Priority Data

Nov. 20, 2002 (NL) .................................... 1021957

(51) Int. Cl.
*G01N 19/02* (2006.01)
*G01N 3/56* (2006.01)
(52) U.S. Cl. .......................... 73/9; 73/7; 73/10; 73/866
(58) Field of Classification Search .................... 73/7, 73/9, 10, 866
See application file for complete search history.

(56) References Cited

U.S. PATENT DOCUMENTS 2,638,776 A * 5/1953 Aines ............................... 73/7

(Continued)

FOREIGN PATENT DOCUMENTS

EP 264526 A2 * 4/1988

(Continued)

OTHER PUBLICATIONS

Medoff, Howard, "Problems in Defining and Measuring Friction on Natural and Artificial Playing Surfaces", 1995, IEEE, pp. 171-174.*
Monckton et al., "Design and Development of an Automated Footwear Testing System", 2002, IEEE, pp. 3684-3689.*

*Primary Examiner*—Hezron Williams
*Assistant Examiner*—David A. Rogers
(74) *Attorney, Agent, or Firm*—Jacobson Holman PLLC

(57) ABSTRACT

The present invention relates to a device for measuring the static and/or dynamic friction coefficient of a surface, in particular a natural or artificial grass surface, which device comprises a housing placed on supports, which is to be positioned on the surface to be examined; a rotatable shaft, which is vertically disposed in said housing; a body connected to the end of said shaft that faces towards the surface, which body comprises a contact surface which can be brought into contact with the surface to be examined; as well as measuring means for measuring, during operation, the torque caused by the friction between the surface to be examined and the contact surface of the rotating body. The object of the present invention is to provide a device for measuring the static and/or dynamic friction coefficient of a surface which provides a more reliable and reproducible measuring result and which is furthermore user-friendly and easy to transport. According to the invention, the device is to that end characterized in that the contact surface of the body is in line with the axis of rotation of the rotatable shaft.

13 Claims, 2 Drawing Sheets

U.S. PATENT DOCUMENTS

| | | | |
|---|---|---|---|
| 3,516,281 A * | 6/1970 | Taub | 73/7 |
| 3,518,872 A * | 7/1970 | Tiner et al. | 73/9 |
| 3,975,940 A * | 8/1976 | Brungraber | 73/9 |
| 4,051,713 A * | 10/1977 | Bao et al. | 73/9 |
| 4,081,989 A * | 4/1978 | Majcherczyk | 73/9 |
| 4,096,733 A * | 6/1978 | Cohen | 73/7 |
| 4,130,007 A * | 12/1978 | Hayashi | 73/7 |
| 4,194,387 A * | 3/1980 | Hofbauer et al. | 73/9 |
| 4,327,572 A * | 5/1982 | Pitman et al. | 73/7 |
| 4,432,223 A * | 2/1984 | Paquette et al. | 73/7 |
| 4,594,878 A * | 6/1986 | Abe et al. | 73/9 |
| 4,633,702 A * | 1/1987 | Kaiser et al. | 73/9 |
| 4,712,418 A | 12/1987 | Augustin | |
| 5,195,357 A * | 3/1993 | Takino et al. | 73/9 |
| 5,259,236 A * | 11/1993 | English | 73/9 |
| 5,576,478 A * | 11/1996 | Brungraber | 73/9 |
| 6,289,743 B1 * | 9/2001 | Norton | 73/847 |
| 6,349,587 B1 * | 2/2002 | Mani et al. | 73/9 |
| 6,679,106 B1 * | 1/2004 | Abe et al. | 73/105 |
| 7,000,451 B1 * | 2/2006 | Wegand et al. | 73/9 |
| 2003/0101793 A1 | 6/2003 | Evans | 73/9 |
| 2004/0187556 A1 * | 9/2004 | Abe et al. | 73/9 |

FOREIGN PATENT DOCUMENTS

| | | | |
|---|---|---|---|
| FR | 2751748 | | 1/1998 |
| GB | 1540982 A | * | 2/1979 |
| GB | 2358931 A | | 8/2001 |
| JP | 57125832 A | * | 8/1982 |
| JP | 60088352 A | * | 5/1985 |
| JP | 02021240 A | * | 1/1990 |
| JP | 04359134 A | * | 12/1992 |
| WO | WO02/63279 | | 8/2002 |

* cited by examiner

DEVICE FOR MEASURING THE STATIC AND/OR DYNAMIC FRICTION COEFFICIENT OF A SURFACE

This is a nationalization of PCT/NL03/000639 filed Sep. 16, 2003 and published in English.

DESCRIPTION

The present invention relates to a device for measuring the static and/or dynamic friction coefficient of a surface, in particular a natural or artificial grass surface, which device comprises a housing placed on supports, which is to be positioned on the surface to be examined; a rotatable shaft, which is vertically disposed in said housing; a body connected to the end of said shaft that faces towards the surface, which body comprises a contact surface which can be brought into contact with the surface to be examined; as well as measuring means for measuring, during operation, the torque caused by the friction between the surface to be examined and the contact surface of the rotating body.

The use of artificial grass as a substitute for natural grass for various outdoor sports has received a lot of attention for a number of years already. Artificial grass lawns usually consist of fibres of various kinds of synthetic material, which are fixed to a mat of a carrier material by tufting or otherwise.

Having a knowledge of the properties and the behaviour of this kind of artificial grass is becoming more and more important, now that also applications such as soccer fields are being considered. In order to make fields of artificial grass in particular suitable for these applications as well, a number of relevant properties thereof need to be further improved. Especially the grip of the sports shoe on such a field and the sliding properties are to be considered in this connection. A safe artificial grass lawn should optimally spare the player's feet. In order to prevent injuries, the friction of the artificial grass should not be too high, whilst on other hand an insufficient degree of grip/friction between the player's foot/shoe and the artificial grass surface is undesirable.

Several instruments and methods for measuring the parameters that influence the playing characteristics of fields of artificial grass and thus acquiring a greater perception of these characteristics in comparison with natural grass and for using the measured parameters in the new developments of artificial grass have been proposed already. A measuring instrument as referred to in the introduction is known, for example from FR-A-2751748. The body comprising the contact surface is mounted on a rod, which rod is disposed perpendicularly to the vertical, rotatable shaft. The body is "dragged" across the surface to be examined. Furthermore, the force with which the body presses on the surface can be adjusted by means of an intricate linkage.

In practice it has become apparent, however, that the results and the ease of use of such a measuring device according to FR-A-2751748 are not fully satisfactory. In addition to being complicated, the measuring construction that is used therein is sensitive to wear and liable to mechanical deformations and loads that have an adverse effect on the measurement.

The object of the present invention is to provide a device for measuring the static and/or dynamic friction coefficient of a surface which provides a more reliable and reproducible measuring result and which is furthermore user-friendly and easy to transport.

In order to accomplish that objective, the device according to the invention is characterized in that the contact surface of the body is in line with the axis of rotation of the rotatable shaft.

When the player turns about his foot during the game, large forces are exerted on the player's ankle and the knee. In addition to that, the playing field should not be too rough, but it should not be too greasy, either, in order to minimize the risk of injuries and the like for the player. With the present construction of the device according to the invention, the way a player turns or rotates about his foot is simulated in a more precise manner, as a result of which are more precise perception of the characteristics of the field on the game is obtained.

This aspect, as well as the simplified construction, with the rotatable shaft placing a direct load on the surface to be examined, provides a more accurate and reproducible measurement in comparison with the known measuring instruments. In addition to that, the present construction is less liable to wear and to mechanical deformations, which has a positive effect not only on the life but also on the measuring result.

A specific, special embodiment of the device according to the invention is characterized in that the shaft is freely movable in vertical direction within the housing, and more in particular loading means can be placed on the end of the shaft remote from the surface. Said loading means may comprise weights.

This makes it possible to press the vertical shaft that is freely movable within the housing against the surface to be examined with varying weights, so as to subject the surface to measurements under different weight loads. This makes the device versatile in use, thanks to its simple construction, wherein the surface to be examined can be subjected to various measurements under varying circumstances (for examples simulations of players having varying weights).

Thus, the more true-to-life simulation measurements will result in a more precise perception of the interaction between the players and the artificial grass lawn.

The body can be detached from the shaft for the purpose of adjusting a specific position of the measuring device for a different measuring situation.

In order to create a measuring situation which is a more true-to-life approximation of the practical situation, the body takes up an inclined position with respect to the surface to be examined. According to one embodiment of the invention, said inclined position of the body is adjustable.

More in particular, said body is shaped as a foot or shoe, with the ball of the foot forming the contact surface of said body. With this embodiment an even more true-to-life simulation of the practical situation is achieved, since it is now possible with the device according to the invention to simulate the influence (the grip as well as the static and dynamic coefficients of friction) of the surface on a player's foot.

In one specific embodiment, the measuring means comprise at least one torsion measuring device.

According to the invention, the supports are detachable so as to enable a quick assembly and disassembly of the measuring instrument and to enable easy transport thereof.

According to the invention, in order to enable a maximally static measurement without any risk of slip between the housing and the surface to be examined, said supports are provided with means for increasing the friction, which means are more in particular embodied as studs, such as the studs used in sports shoes.

The invention will now be explained in more detail with reference to the drawing, in which.

Like parts are indicated by the same numerals in the two Figures.

The device is made up of a housing 10, which can be placed on a surface 1 to be examined via supports 11a-11c. The surface 1 to be examined may be a natural grass sports field or an artificial grass sports field. Especially such artificial grass sports field are increasingly being used for practising sports that are usually played on natural grass sports fields. Such sports include field hockey, soccer and the like. The device can also be used on so-called tartan tracks (athletics tracks and tennis courts).

When artificial grass sports fields are used for such intensive and physical contact sports, having a knowledge of the properties and the behaviour of this kind of artificial grass surfaces is indispensable. It is necessary to measure the properties of such artificial grass sports fields, not only in order to be able to compare these sports fields with natural grass sports fields, but also because such measured parameters are important in connection with the development of a new generation of artificial grass sports fields. Last but no least, having a knowledge of the specific properties of artificial grass sports field is indispensable because it is possible in this manner not only to come as close to the playing characteristics of natural grass as possible but also to minimize the risk of the players sustaining injuries.

Figure 1:
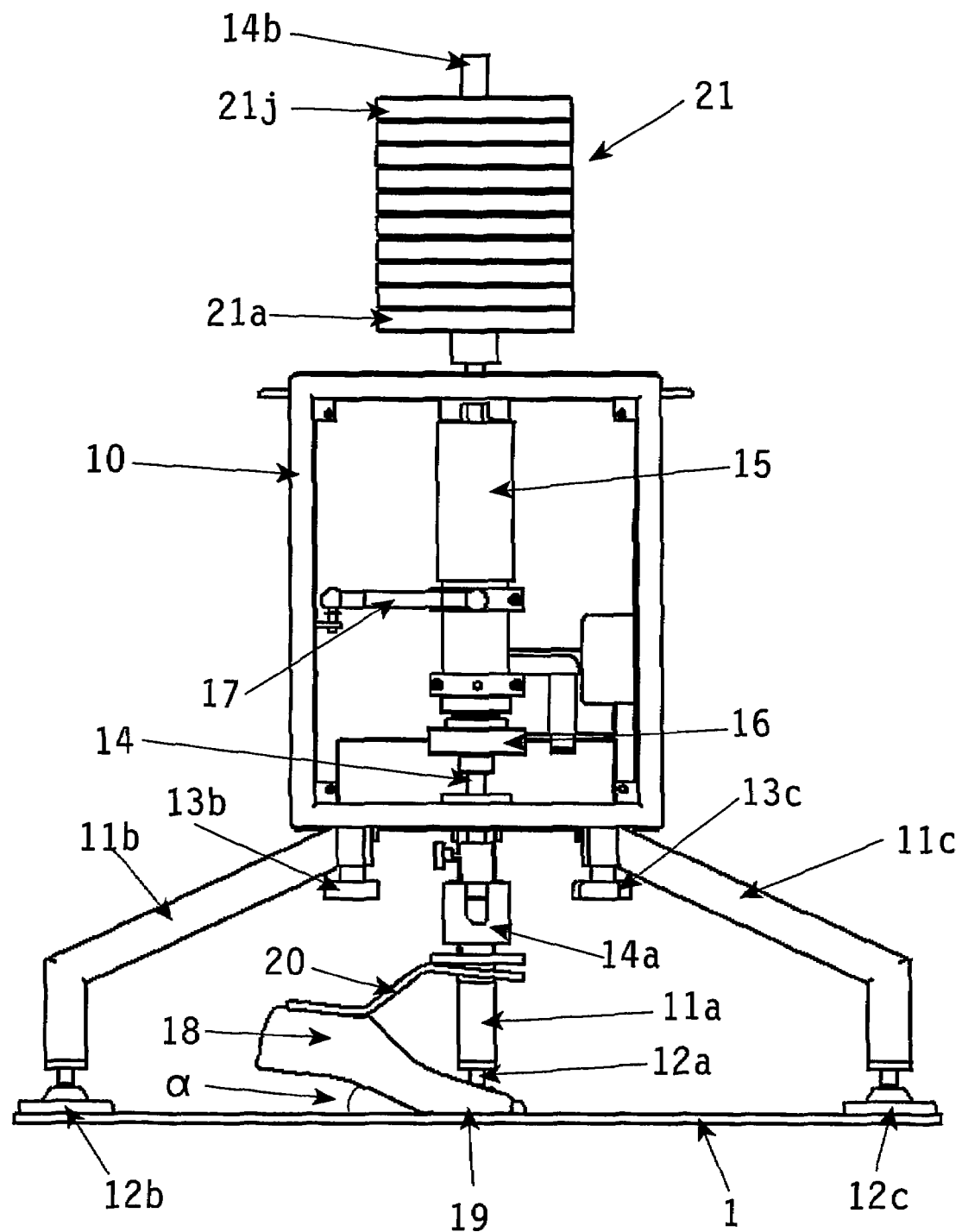
FIG. 1 is a side elevation of an embodiment of a device according to the invention.
Figure 2:
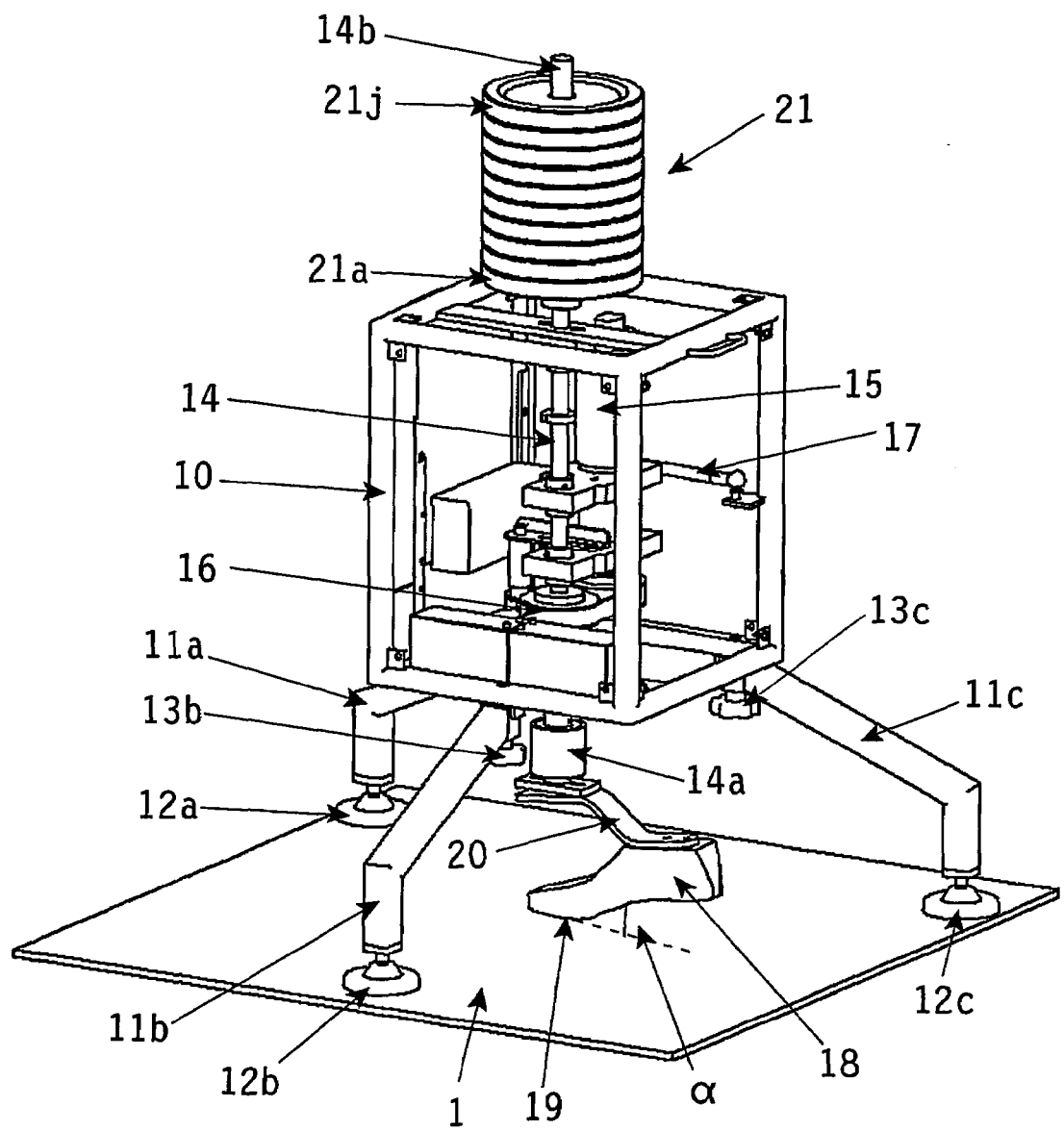
FIG. 2 is a perspective view of the embodiment of the device according to FIG. 1.

With the embodiment as shown in FIGS. 1 and 2 of a device for measuring properties of a surface 1 to be examined, more in particular of an artificial grass sports field, but also of a natural grass sports field, it is specifically the friction torque (friction and grip) between the player and the sports field which occurs in situations in which a rotational movement is made that is measured. Think for example of the quick turning or rotating of a player about one leg, wherein the leg and more specifically the ankle and the knee may be exposed to considerable forces.

The device that is shown in FIGS. 1 and 2 rests on the surface 1 to be examined via the supports 11a-11c. Disposed within the housing 10 is a vertical shaft 14, which can be rotated at any desired speed by means of a suitable drive unit 15, for example an electric motor, via a belt transmission 16. The vertical shaft 14 may be rotated at a constant speed, but it is also possible to drive the vertical shaft 14 at a higher or a lower speed so as to simulate particular, specific situations in the game.

To that end the device is provided with suitable control and regulating means, for example a computer which may be disposed within the housing 10 or which can be placed as a separate unit beside the device on the surface 1 to be examined. Said control and regulating apparatus (a computer, for example) may also be provided with suitable processing means (software, for example) for processing the measuring results and presenting said measuring results to the user.

Preferably, the vertical shaft 14 is freely movable in vertical direction within the housing 10 to a certain extent, so that said housing rests on the surface 1 to be examined under the influence of the force of gravity. More in particular, a body 18 is present on the free end 14a of the shaft 14 that faces towards the surface 1, which body comprises a contact surface 19 that rests on the surface 1 to be examined.

The body 18 may have the shape of a foot, which is connected to the lower end 14a of the shaft 14 by means of a mounting plate 20.

In accordance with the invention, the contact surface 19 of the body 18 is in line with the axis of rotation of the shaft 14 that is vertically disposed within the housing 10. This construction enables a more realistic and accurate simulation of the way a player turns or rotates about his foot, as a result of which a more accurate measurement of the specific properties of the surface 1 to be examined is obtained. This makes it possible to use the obtained measuring results relating to the friction coefficient of the surface in the direction of rotation for comparing the surface to be examined (an artificial grass sports field, for example) with other surfaces (a natural grass sports field, for example). Furthermore, the greater accuracy and reproducibility of the obtained measuring results make it possible to use said results in the development of new generations of artificial grass sports fields.

Another advantage of the construction according to the invention as disclosed in FIGS. 1 and 2 is the fact that the extent to which wear and mechanical deformations occur is reduced as a result of the relevant parts being arranged around one axis of rotation. Thus, not only the life of said parts is extended, but in addition the measuring results are not adversely affected thereby.

As a result of the vertical shaft 14 being rotated by the drive unit 15 and the consequent rotation of the contact surface 19 of the body 18 on the surface 1 to be examined, a counter torque or torsion is generated, which torsion is detected by suitable measuring means, for example one or more torsion measuring devices arranged at different positions on the shaft, and fed to the control and measuring apparatus (the computer, for example) for further processing and presentation. In order to prevent, the moving parts in the housing 10 from generating a counter torque that might have an adverse effect on the measuring results, the drive motor 15 is fixedly mounted in the housing 10 by means of a mounting rod 17. Thus, the operation of the motor 15 will not influence the rotation of the vertical shaft 14 and the final measuring result. The measurement friction torque of the shaft provides a direct perception of the frictional force produced during rotation between the contact surface 19 of the body 18 and the surface 1 of the (artificial) grass sports field.

Although the body 18 is schematically represented in the form of a foot in FIGS. 1 and 2, it is also possible to use other shapes. A sports shoe (not shown) may be put on the foot 18, in which case the surface 19, via which the shoe makes contact with the surface 1 to be examined, may be provided with studs, spikes or "blades" (moon-shaped or oval studs), for example.

In order to prevent the device from moving over the supporting surface 1 while the body 18 is being rotated, the supports 11a-11c may be provided with means 12a-12c for increasing the friction, which means may in particular consist of or be provided with studs or spikes such as those used with normal sports shoes. The circle described by the supports 11a-11c may be selected such that the moment of friction between the body 18 and the surface 1 to be examined will at all times be lower than the maximum moment of friction between the supports 11a-11c and the surface 1. As a result, the amount of slip that occurs between the device and the surface 1 will be minimal.

In order to enable easy transport of the device, the supports 11a-11c are connected to the housing 10 by means of screws 13a-13c.

Furthermore it is readily possible to remove the body 18 from the lower end 14a of the shaft 14, which is done for the purpose of protecting the body 18 during transport or re-setting the device according to the invention for a different type of body 18 having a different shape (another type of shoe, for example). This makes it possible to carry out measurements on the surface 1 under different circumstances.

The device may be vertically adjustable with respect to the body 18.

Preferably, the body 18 takes up an inclined position with respect to the surface 1 to be examined, in which case a constant angle of inclination α is used. After all, the inclined position of the body 18 relative to the surface 1 leads to a more accurate simulation of the actual situation, since a player usually rests on the ball of his foot when making a turning or rotating movement. It is also possible, however, to set said inclined position and, thus the angle α relative to the surface 1 to be examined, so as to simulate different situations in the game and thus carry out measurements under different circumstances.

As already noted before, the rotational speed of the shaft 14 and the body 18 is constant, amounting to 2-11 revolutions per minute (rpm), depending on the situation in the game that is to be simulated. The rotational speed may also be increased or decreased to a particular number of revolutions, however, likewise in dependence on the situation in the game that is to be simulated and examined. The measurement of the torque as exerted on the surface 1 by the body 18 is measured in the shaft 14 by means of suitable torsion measuring devices, with the body 18 preferably being rotated through 90° during a measurement. A rotational movement of this magnitude is the most frequent rotational movement that players make on a sports field during normal situations in the game. Also other rotational movements are possible, however, depending on the measuring situation that is to be examined.

As already noted before, the shaft 14 is freely movable within the housing 10, and according to the invention it may be provided with loading means 21 near its free end 14b, which loading means are made up of one or more weights 21a-21j. Thus it is possible to press the shaft 14 and the body 18 comprising the contact surface 19 down on the surface to be examined with a specific weight/load. This makes it possible to obtain measuring results for respective fictional players having different weights. This renders the device according to the invention more versatile in use, whilst in addition all kinds of different situations are simulated more accurately. After all, a player will place a large part of his weight on the foot he stands on when turning or rotating about his foot.

It will be apparent that the device according to the invention as shown in FIGS. 1 and 2 provides a versatile measuring instrument, by means of which a great number of different situations in the game can be simulated in the most natural manner possible. Consequently, the measuring results thus obtained provide a more true-to-life indication with regard to, the rotational interaction between the player's foot and an artificial grass sports field, for example, which measuring results enable a better comparison with a natural grass sports field.

Furthermore it is possible, using the measuring instrument according to the invention, to measure the dynamic friction of the surface to be examined by imposing an acceleration or deceleration on the body 18 during rotation of the shaft 14.

The invention claimed is:

1. A device for measuring the static and/or dynamic friction coefficient of a surface comprising:
    a housing placed on supports, which is to be positioned on the surface to be examined;
    a rotatable shaft, which is vertically disposed in said housing;
    a body connected to the end of said shaft that faces towards the surface, which body comprises a contact surface which can be brought into contact with the surface to be examined; and
    measuring means for measuring, during operation, the torque caused by the friction between the surface to be examined and the contact surface of the rotating body, wherein the contact surface of the body is in line with the axis of rotation of the rotatable shaft.

2. A device according to claim 1, wherein said shaft is freely movable in vertical direction within the housing.

3. A device according to claim 1, wherein said body can be detached from said shaft.

4. A device according to claim 1, wherein the measuring means comprises at least one torsion measuring device.

5. A device according to claim 1, wherein said supports are detachable.

6. A device according to claim 1, wherein said supports are provided with means for increasing the friction between the supports and the surface to be measured.

7. A device according to claim 6, wherein said means for increasing the friction are embodied as studs.

8. A device according to claim 1, wherein loading means can be placed on the end of the shaft remote from the surface.

9. A device according to claim 8, wherein said loading means comprises weights.

10. A device according to claim 1, wherein said body takes up an inclined position with respect to the surface to be examined.

11. A device according to claim 10, wherein the inclined position of the body is adjustable.

12. A device according to claim 1, wherein said body has the shape of a foot.

13. A device according to claim 12, wherein the ball of the foot forms the contact surface of said body.

* * * * *